(12) United States Patent
Ono et al.

(10) Patent No.: US 11,273,438 B2
(45) Date of Patent: Mar. 15, 2022

(54) SAFETY CABINET

(71) Applicant: Hitachi Industrial Equipment Systems Co., Ltd., Tokyo (JP)

(72) Inventors: Keiichi Ono, Tainai (JP); Hirotoshi Sato, Tainai (JP)

(73) Assignee: HITACHI INDUSTRIAL EQUIPMENT SYSTEMS CO., LTD., Tokyo (JP)

( * ) Notice: Subject to any disclaimer, the term of this patent is extended or adjusted under 35 U.S.C. 154(b) by 287 days.

(21) Appl. No.: 16/474,522

(22) PCT Filed: Feb. 19, 2018

(86) PCT No.: PCT/JP2018/005750
§ 371 (c)(1),
(2) Date: Jun. 27, 2019

(87) PCT Pub. No.: WO2018/230043
PCT Pub. Date: Dec. 20, 2018

(65) Prior Publication Data
US 2020/0023349 A1    Jan. 23, 2020

(30) Foreign Application Priority Data

Jun. 14, 2017   (JP) .............................. JP2017-116368

(51) Int. Cl.
*B01L 1/00*  (2006.01)
*B08B 15/02*  (2006.01)
*F24F 3/163*  (2021.01)

(52) U.S. Cl.
CPC .................. *B01L 1/50* (2013.01); *B01L 1/00* (2013.01); *B08B 15/02* (2013.01); *F24F 3/163* (2021.01);

(Continued)

(58) Field of Classification Search
CPC .... F24F 3/163; B01L 1/50; B01L 1/00; B01L 2200/082; B01L 2300/0681; B08B 15/023; B08B 15/02; C12M 1/00
(Continued)

(56) References Cited

U.S. PATENT DOCUMENTS 4,098,174 A   7/1978  Landy
9,095,802 B2 *  8/2015  McCarthy .......... B01D 46/0091
(Continued)

FOREIGN PATENT DOCUMENTS

CN    101131395 A    2/2008
CN    104511318 A    4/2015
(Continued)

OTHER PUBLICATIONS

Chinese Office Action issued in corresponding Chinese Patent Application No. 201880004962.0, dated Dec. 1, 2020 w/English translation.

(Continued)

*Primary Examiner* — Jessica Yuen
(74) *Attorney, Agent, or Firm* — McDermott Will & Emery LLP

(57) ABSTRACT

Provided is a safety cabinet that prevents oversights in airtightness tests and HEPA filter penetration ratio tests even if a pathogen or the like leaks from a workspace wall surface in the interior of the safety cabinet. The safety cabinet includes: a work surface at the bottom of a workspace; a front panel at the front of the workspace; a work opening section below the front panel; and a first air purification means that filters exhaust air that is air discharged from within the workspace. The safety cabinet is characterized in that the non-workspace sides of a side wall surface and a back wall surface of the workspace are formed by an outer wall of a device with prescribed airtightness performance.

1 Claim, 9 Drawing Sheets

(52) U.S. Cl.
　　CPC .　*B01L 2200/082* (2013.01); *B01L 2300/0681* (2013.01)

(58) Field of Classification Search
　　USPC ........................................................ 454/187
　　See application file for complete search history.

(56) References Cited

U.S. PATENT DOCUMENTS

| | | | |
|---|---|---|---|
| 10,507,500 B1* | 12/2019 | Hunter | ................ F24F 11/0001 |
| 2006/0150593 A1 | 7/2006 | Ono | |
| 2018/0214861 A1 | 8/2018 | Ono et al. | |

FOREIGN PATENT DOCUMENTS

| | | |
|---|---|---|
| JP | 50-068400 U1 | 6/1975 |
| JP | 52-126281 A | 10/1977 |
| JP | 54-132200 U1 | 9/1979 |
| JP | 60-120219 A | 6/1985 |
| JP | 1-288342 A | 11/1989 |
| JP | 9-168993 A | 6/1997 |
| JP | 2003-254574 A | 9/2003 |
| JP | 2004181434 A | 7/2004 |
| JP | 2008295448 A | 12/2008 |
| WO | 2016079777 A1 | 5/2016 |

OTHER PUBLICATIONS

International Search Report issued in corresponding PCT/JP2018/005750, dated May 22, 2018, with English translation.

Japanese Office Action issued in corresponding Japanese Patent Application No. 2017-116368, dated Mar. 31, 2020, with English translation.

"Class II biological safety cabiinets," JIS K3800:2009, with partial translation.

* cited by examiner

SAFETY CABINET

CROSS REFERENCE

This application is the U.S. National Phase under 35 U.S.C. § 371 of International Application No. PCT/JP2018/005750, filed on Feb. 19, 2018, which claims the benefit of Japanese Application No. 2017-116368, filed on Jun. 14, 2017, the entire contents of each are hereby incorporated by reference.

TECHNICAL FIELD

The present invention relates to a safety cabinet that handles pathogen or the like in a device.

BACKGROUND ART

A biohazard countermeasure class II cabinet (hereinafter referred to as "safety cabinet") is used for research of infectious disease, pharmaceutical research or manufacturing, aseptic preparation and adjustment of anticancer drugs. The safety cabinet supplies clean air in which dust, pathogen, and the like are filtered by a HEPA filter or UPLA filter for blow-off from an upper blow-off part of a workspace formed in a device, sucks air of a laboratory in which the safety cabinet is disposed and air of the workspace together, from a work opening section formed at a front of the workspace and a work table front suction port formed in front of the work table which is a bottom of the workspace, and generates an inflow air flow in the work opening section. Further, when the sucked air is exhausted out of the safety cabinet, air containing pathogen or the like is filtered with an exhaust HEPA filter or an UPLA filter. The HEPA filter is an abbreviation of High Efficiency Particulate Air Filter, and the UPLA filter is an abbreviation of Ultra Low Penetration Air Filter. The inflow air flow generated at the work opening section prevents pathogen or the like handled in the workspace from leaking out of the safety cabinet and causing infection to researchers and spreading to the environment. In the case of a class II cabinet, it is used in a wide range of fields because a so-called "aseptic operation" in which clean air is supplied to the workspace is available.

The performance for preventing pathogen or the like handled by the safety cabinet from leaking out of the workspace is the air speed of the clean air blown out to the workspace, the magnitude of the air speed of the inflow air flow generated at the work opening section and a balance of both. Further, if there is a leakage in the HEPA filter/UPLA filter, the leakage causes a problem that pathogen or the like may leak out of the safety cabinet through the HEPA filter/UPLA filter or the clean air cannot be supplied to the workspace. Furthermore, if there is a hole on an outer wall of the safety cabinet, since there is a possibility that pathogen or the like may leak, the tightness of the structure is required. When the safety cabinet is used, the HEPA filter/UPLA filter is clogged, which reduces the blow-off air speed and the air speed of the inflow air flow, and there is a possibility that pathogen or the like may leak from the workspace, or by opening the holes in the HEPA filter/UPLA filter, there is a possibility that pathogen or the like may leak. The same is also applied to a case where the hole is formed on the outer wall of the safety cabinet. Therefore, periodic inspection is required to maintain the performance of the safety cabinet.

As a background art in the present technical field, there is JP 2004-181434 A (Patent Document 1). Patent Document 1 discloses a method of leading air in a negative pressure space surrounding a workspace for handling the pathogen or the like to an exhaust HEPA filter and a blowing unit, and purifying the air with the exhaust HEPA filter.

CITATION LIST

Patent Document

Patent Document 1: JP 2004-181434 A

SUMMARY OF THE INVENTION

Problems to be Solved by the Invention

In the safety cabinet of Patent Document 1, a method is described in which the air sucked into the space of a back surface and both sides of the workspace is purified by the exhaust HEPA filter and discharged out of the device. There is a possibility that the air on the back surface and both sides of the workspace contains pathogen or the like that leaks from a gap of the workspace wall surface. The pathogen or the like is recovered by the HEPA filter before being discharged out of the safety cabinet.

According to the JP biohazard countermeasure class II cabinet standard, JIS K3800: 2009, the required performance of a safety cabinet and a test method are disclosed. The penetration ratio of the HEPA filter is described as the required performance for managing the prevention of the leakage of pathogen or the like from the HEPA filter. The method is that a suction port of a detector for penetration ratio measurement is kept within 25 mm from the filter surface and the entire surface of the filter blow-off surface is scan-tested for the entire filter medium of the downstream side of the HEPA filter, and the dust concentration measured on the downstream side of the HEPA filter is divided by the dust concentration on the upstream side of the HEPA filter to obtain the penetration ratio. The penetration ratio in the scanning test is managed not to exceed 0.01% in aerosol particles of 0.3 µm at all points of the filter.

Due to the structure of the safety cabinet, the penetration ratio when the scanning test is not possible is 0.005% or less at a position before the air filtered by the HEPA filter mixes with other air flow. According to the US safety cabinet standard, NSF/ANSI 49-2014 Biosafety Cabinetry, even if the UPLA filter is used, it is assumed that there is no site in which the penetration ratio exceeds 0.01% in the aerosol particles of 0.3 µm, and the penetration ratio test method and determination criteria are the same even when the HEPA filter or the UPLA filter is used.

In addition, according to JIS K3800: 2009, airtightness as a required performance in which pathogen or the like does not leak from the outer wall of the safety cabinet is disclosed. The test method is to seal a front opening section (a work opening section) and the exhaust port of the safety cabinet, if necessary, the suction port, pressurize the inside of the safety cabinet to 500 Pa, using the compressed air, and check for the presence or absence of leakage from the outer wall. The penetration ratio test of the HEPA filter and the airtightness test of the safety cabinet are periodic inspection items required to maintain the performance of the safety cabinet that prevents the leakage of pathogen or the like in combination with the air speed test.

The outer wall of the safety cabinet is a part in which the periphery of the safety cabinet contacts with air of the laboratory when the safety cabinet is disposed in the laboratory. Because covers for design attached to the safety cabinet without the airtightness performance of JIS K3800: 2009 do not have the airtightness performance, there is a possibility that pathogen or the like may leak. Thus, such covers are excluded from the definition of the outer wall. Further, the outer wall of the safety cabinet is connected to the wall surface in the workspace of the safety cabinet at the work opening section on the front of the safety cabinet, but the definition of the outer wall is separated from the wall surface in the workspace at the work opening section. A front panel for the experimenter to look into the workspace is formed at the upper part of the work opening section. One side of the front panel forms one side in the workspace, and the other side thereof is connected to the outer wall of the safety cabinet, but the front panel is not defined as a part of the outer wall of the safety cabinet but is defined as the front panel. The method of sealing the work opening section in the airtightness test of JIS K3800: 2009 includes a method of using the front panel and a method of sealing the work opening section with a test cover including the front panel and the work opening section. When different materials are configured to be stacked on the outer side of the safety cabinet and the inner wall of the workspace, a space may be created between the two materials. In this case, the airtightness performance of JIS K3800: 2009 may be maintained outside or on the inner wall of the workspace.

There is a plurality of types and kinds of structures in the safety cabinet as described in JIS K3800: 2009. FIG. 9 is a cross-sectional view illustrating the kinds of the safety cabinet of related art.

When handling pathogen or the like in the workspace, it is necessary to filter the pathogen or the like by the HEPA filter from the air leaked from the wall surface of the workspace before discharging out of the safety cabinet. Whether pathogen or the like is filtered by the HEPA filter can be checked by the penetration ratio test of the HEPA filter. If the non-workspace side of the workspace inner wall surface is a safety cabinet outer wall, it is possible to check by the airtightness test that there is no leakage in the outer wall.

In the case of the safety cabinets of symbols A, B, D and F in FIG. 9, since a back flow path 108 of the workspace back surface is supplied with air blown out of the blower, the pressure becomes higher than the workspace. If a leakage occurs on the back surface of the workspace, in the symbols A and B, pathogen or the like handled in the workspace and dust generated from the blower enter the workspace, and in the symbols D and F, dust generated by the blower enters the workspace. Since JIS K3800: 2009 does not stipulate that dust generated by the blower enters the workspace, the symbol D exists in the standard. However, in recent years, since a clean space for aseptic operation is used in various fields, in some cases, dust generated by the blower may not be required to enter the workspace.

When performing the penetration ratio test of the HEPA filter, the downstream side of the HEPA filter of symbol D and an exhaust HEPA filter 101a of symbol F is a negative pressure space surrounded by the safety cabinet outer wall. Since an ambient air dust enters from the insertion port of the arm, it is difficult to insert an arm with a detector for penetration ratio test into a negative pressure space and conduct a scanning test. In this case, as a case where the scanning test is not possible, the penetration ratio of 0.005% or less is managed at the representative point. Although it is considered as a representative point, because the sensitivity of the penetration ratio differs depending on the distance from the HEPA filter blow-off surface and the mixed state of the air flow, it is necessary to perform measurement at a representative point recommended by the manufacturer.

In the drawing of the symbol F, an exhaust blower 112 is disposed in the safety cabinet, but the cabinet of type B2 of the symbol F is required to exhaust the air outdoors. Thus, there is a case where the exhaust blower 112 is prepared and exhausted on the building side and is not placed in the safety cabinet. In this case, the back flow path 108 of the workspace back surface is under negative pressure by the suction of the building exhaust blower. If a leakage occurs on the workspace back surface in this structure, pathogen or the like handled in the workspace leaks into the back flow path 108. The leaked pathogen or the like is exhausted without being collected by the HEPA filter. In the airtightness test of this structure, a front opening section (a work opening section), the suction port including a blow-off blower 111, and an exhaust port 114 are sealed, and the inside of the safety cabinet is pressurized to 500 Pa using compressed air to check the presence or absence of leakage from the outer wall. However, as a leakage of the workspace back surface is inside the sealed safety cabinet, the leakage is overlooked.

An object of the present invention is to provide a safety cabinet which prevents the leakage from oversight in the airtightness test and the HEPA filter penetration ratio test, even if pathogen or the like leaks from the workspace wall surface inside the safety cabinet.

Solutions to Problems

In an example of the safety cabinet of the present invention for solving the above problems, there is provided a safety cabinet which has a work surface on a bottom of a workspace, a front panel at a front of the workspace, and a work opening section below the front panel, and has a first air purification means configured to filter exhaust air for exhausting air in the workspace, wherein non-workspace sides of a side wall surface and a back wall surface of the workspace are formed by an outer wall of a device with prescribed airtightness performance.

Effects of the Invention

According to the present invention, the possibility that pathogen or the like leaks from the workspace wall surface or the HEPA filter can be accurately determined by the test method of the safety cabinet.

MODE FOR CARRYING OUT THE INVENTION

Figure 1A:
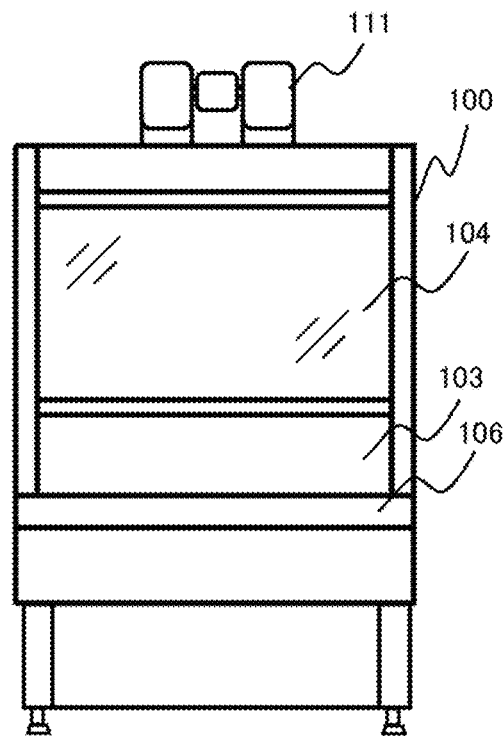
FIG. 1A is an example of an external front view illustrating a safety cabinet of Example 1.

Hereinafter, examples of the present invention will be described using the drawings. In the drawings illustrating the examples, the same components are denoted by the same names and symbols as much as possible, and the repetitive description thereof will not be provided.

Example 1

Figure 1B:
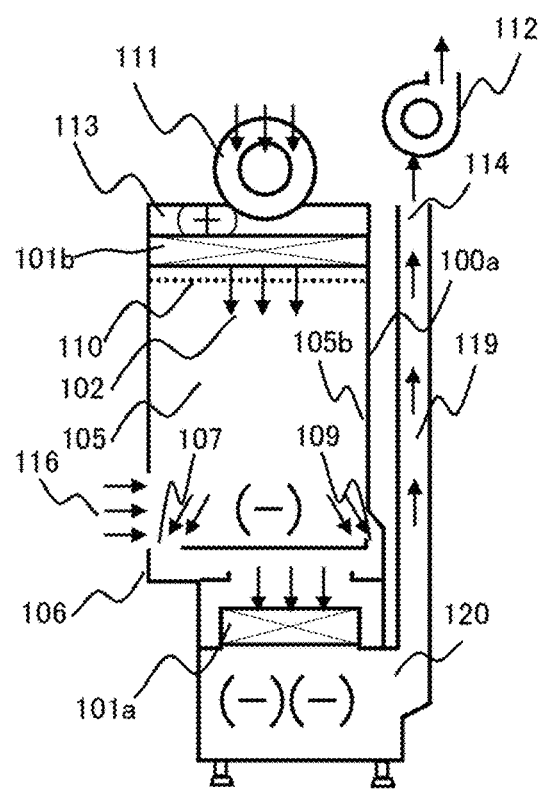
FIG. 1B is an example of a side cross-sectional view illustrating the safety cabinet of Example 1.
Figure 2A:
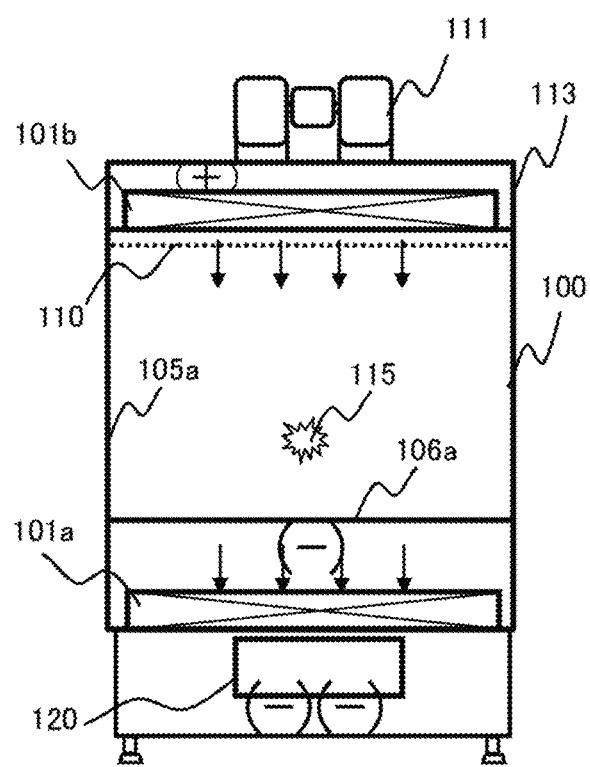
FIG. 2A is an example of a front cross-sectional view illustrating the safety cabinet of Example 1.
Figure 2B:
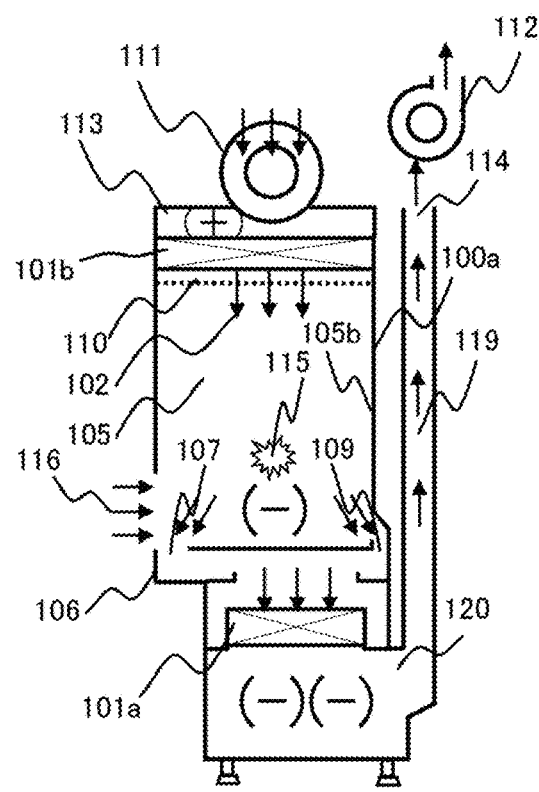
FIG. 2B is an example of a side cross-sectional view illustrating the safety cabinet of Example 1.

FIG. 1A is an example of an external front view illustrating the safety cabinet of Example 1, and FIG. 1B is an example of a side cross-sectional view. Moreover, FIG. 2A is an example of front sectional view which illustrates the safety cabinet of Example 1 at the time of work, and FIG. 2B is an example of side cross-sectional view.

A blow-off blower 111 sucks the air in a laboratory in which a safety cabinet 100 is disposed, and pressurizes a pressure chamber 113. Since the pressure chamber 113 is connected to a blow-off HEPA filter 101b, the air in the laboratory is purified by the blow-off HEPA filter 101b and blown out to a workspace 105 as clean air 102. The blow-off air speed of the clean air 102 blown into the workspace 105 is rectified by a flow straightening plate 110.

The front of the workspace 105 is surrounded by a front panel 104, the side surface thereof is surrounded by a workspace side wall surface 105a, the back surface thereof is surrounded by a workspace back wall surface 105b, and the bottom surface thereof is surrounded by a work surface 106a of a work table 106. A work opening section 103 is formed below the front panel 104. The front panel 104 may be of a sliding type or a flip-up type. A researcher inserts his/her arm from the work opening section 103 into the workspace 105 to handle the pathogen or the like 115. A work table front suction port 107 is formed in front of the work table 106 and below the front panel 104 to suck air in the laboratory and air containing the pathogen or the like 115 of the workspace 105. During the experiment, there is a possibility that air in the laboratory may contain the pathogen or the like 115. This inflowing air is an inflow air flow 116.

A rear suction port 109 is formed at the rear of the workspace 105. The clean air 102 blown out to the workspace 105 and the pathogen or the like 115 handled in the workspace 105 are divided into the work table front suction port 107 and the rear suction port 109 and sucked. Since the sucked air contains the pathogen or the like 115 and dust in the laboratory, it is filtered and exhausted by the exhaust HEPA filter 101a formed below the work table 106. The air filtered by the exhaust HEPA filter 101a enters an exhaust flow path 119 from an exhaust flow path inlet 120, is sucked from the exhaust port 114 by the exhaust blower 112, and is discharged out of the safety cabinet 100.

In this air flow configuration, since both the clean air 102 to be blown out and the inflow air flow 116 entering the safety cabinet 100 from the work opening section 103 are filtered by the exhaust HEPA filter 101a and exhausted from the exhaust port 114, there is no air flow circulating in the safety cabinet 100. This structure is set as a class II type B2 in the safety cabinet standard. When the air flow circulates in the safety cabinet, gaseous substances and radioactive substances which are not collected by the HEPA filter pass through the blow-off HEPA filter 101b and blow out again to the workspace 105. Depending on the experimental contents, in some cases, there is a need to eliminate the re-circulating gaseous substances and radioactive substances. In that case, a safety cabinet 100 of class II type B2 is used. Since a gaseous substance not collected by the HEPA filter is used, a duct is always connected to the exhaust port 114 to exhaust the air outdoors. The gaseous substances are exhausted outdoors, but pathogen or the like 115 is collected by the exhaust HEPA filter 101a.

In addition, the workspace side wall surface 105a, the workspace back wall surface 105b, and the opposite sides of the air flowing surface of the wall surfaces forming the space on the suction sides of the exhaust HEPA filter 101a are formed by the safety cabinet outer wall 100a. Further, the safety cabinet outer wall 100a has prescribed airtightness performance.

Figure 1C:
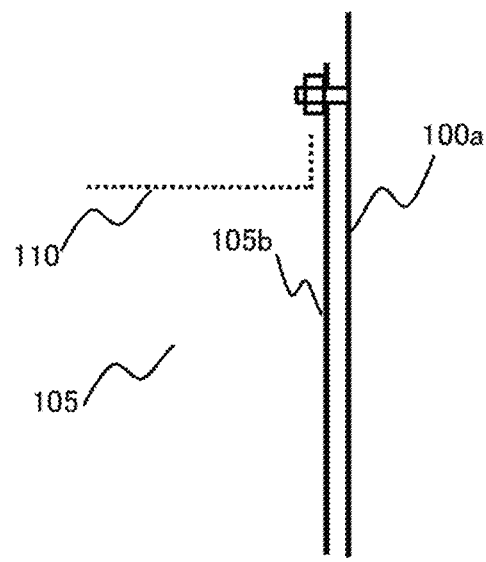
FIG. 1C is an example of a cross-sectional view of an outer wall of the safety cabinet.

FIG. 1C illustrates a partial cross-sectional structural view of the outer wall of the safety cabinet. The workspace back wall surface 105b may be made of a material (such as stainless steel SUS304) resistant to a disinfectant, and a painted steel plate may be used for the safety cabinet outer wall 100a. When different members are connected, they are connected by screws, welding or the like on the opposite side of the workspace 105 of the flow straightening plate 110 or on the opposite side of the workspace 105 of the work surface 106a (not illustrated). An air layer may be formed between the workspace back wall surface 105b and the safety cabinet outer wall 100a, when they are formed of different members. An air layer may be present or in close contact between the workspace back wall surface 105b and the safety cabinet outer wall 100a, but air should not leak from the outer wall 100a. The same also applies to the case of the workspace side wall surface 105a.

Moreover, as a design of the safety cabinet 100, there is a case where a detachable cover is provided. In the definition of the safety cabinet outer wall 100a, a pressure of 500 Pa is applied to the inside of the safety cabinet 100 to perform the airtightness test, and the surface for evaluating the presence or absence of a leakage is set as the safety cabinet outer wall 100a. Therefore, when a leakage is evaluated by foaming of soap water or the like, it is a surface to which soap water is applied or sprayed.

Periodic maintenance is necessary to maintain the ability which confines pathogen or the likes handled by the safety cabinet in the safety cabinet. In order to confine pathogen or the like by air flow, it is important the inflow air flow 116 generated at the work opening section 103, the magnitude of the air speed of the clean air 102 blown out of the flow straightening plate 110 and maintenance of a balance of both. The air speed of the clean air 102 to be blown out may be evaluated near the height of the lower end of the front panel 104 rather than near the flow straightening plate 110. In addition, it is also necessary to check that the exhaust HEPA filter 101a and the blow-off HEPA filter 101b maintain the performance capable of collecting the pathogen or the like. This performance of the HEPA filter is called a penetration ratio. Furthermore, since the air flow containing the pathogen or the like 115 is flowing in the safety cabinet 100, it is necessary to check that a hole is not perforated in the safety cabinet outer wall 100a. This performance is called airtightness.

When checking the penetration ratio of the blow-off HEPA filter 101b, in the operation state of the safety cabinet 100, a ratio of the concentration on the upstream side in which an appropriate simulated dust load is imparted to the upstream side of the blow-off HEPA filter 101b from the suction side of the blow-off blower 111 and the concentration of the simulated dust, on the downstream side, leaking and penetrating to the downstream side of the blow-off HEPA filter 101b is measured as the penetration ratio. According to JIS K3800 standard for safety cabinets, aerosol particles of 0.3 μm are given as a suitable simulated dust load, and the entire surface of the blow-off surface of the blow-off HEPA filter 101b is subjected to a scanning test, and it is checked that there is no region in which the penetration ratio exceeds 0.01%. When performing the scanning test, the flow straightening plate 110 on the downstream of the blow-off HEPA filter 101b is detached, and there is a need to maintain a distance between the blow-off surface of the blow-off HEPA filter 101b and a suction port of a penetration ratio detector (not illustrated) for penetration ratio measurement within 25 mm.

When checking the penetration ratio of the exhaust HEPA filter 101a, an appropriate simulated dust load is applied from the work table front suction port 107 on the upstream side of the exhaust HEPA filter 101a in the operating state of the safety cabinet 100. At this time, if the concentration of the load on the upstream side of the exhaust HEPA filter 101a does not rise to a concentration sufficient for measurement, the load for the penetration ratio test may be supplied from the work table front suction port 107, using a blower of the test (not illustrated). On the downstream side of the exhaust HEPA filter 101a, as in the case of the blow-off HEPA filter 101b, when the distance between the blow-off surface and the suction port of the penetration ratio detector is kept within 25 mm and the scanning test is performed, since the downstream side of the exhaust HEPA filter 101a has a negative pressure compared to the pressure of the laboratory in which the safety cabinet 100 is disposed, an opening section is provided in the safety cabinet outer wall 100a on the downstream side of the exhaust HEPA filter 101a, and when an arm with a penetration ratio detector is inserted, the dust in the laboratory is sucked from the opening section to the downstream side of the exhaust HEPA filter 101a. In this case, since an appropriate scanning test cannot be performed, a penetration ratio of 0.005% or less is checked at a representative point on the basis of the safety cabinet standard of JIS K3800: 2009. When evaluating at a representative point, it is necessary to perform the measurement at a place where the air coming out of the entire blow-off surface of the exhaust HEPA filter 101a mixes sufficiently. In Example 1, the air is sufficiently mixed by flowing through the exhaust flow path 119 located downstream of the exhaust HEPA filter 101a, and the penetration ratio of 0.005% or less can be managed at the representative point of the exhaust port 114.

As a measurement position at a representative point of the exhaust port 114, a penetration ratio measurement hole 118 (not illustrated) may be provided in the exhaust flow path 119.

Figure 3A:
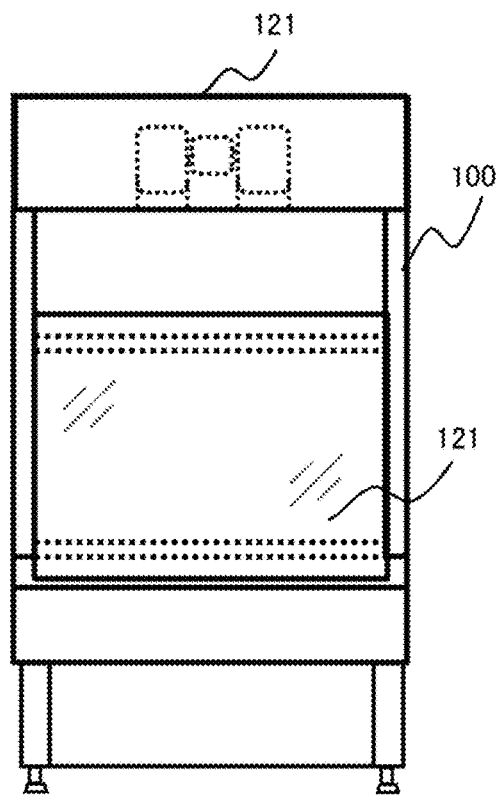
FIG. 3A is an example of an external front view at the time of an airtightness test illustrating the safety cabinet of Example 1.
Figure 3B:
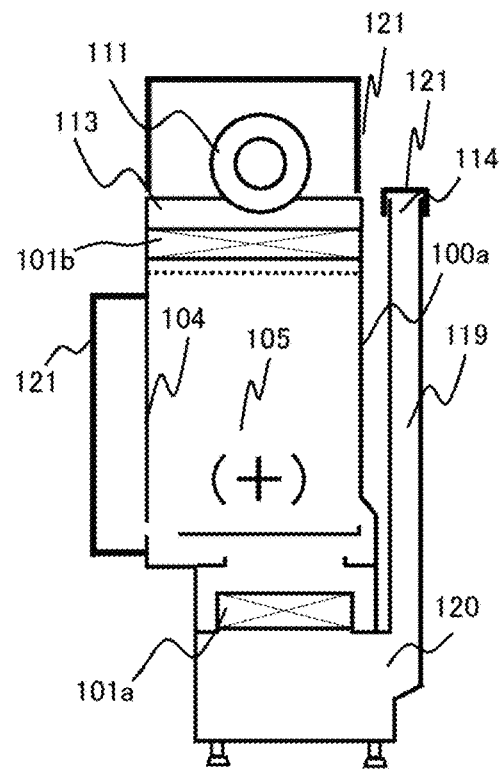
FIG. 3B is an example of a side cross-sectional view at the time of the airtightness test, illustrating the safety cabinet of Example 1.

The example of the external appearance front view at the time of the airtightness test which illustrates the safety cabinet of Example 1 is illustrated in FIG. 3A, and an example of side cross-sectional view is illustrated in FIG. 3B.

As a test method of proving that the pathogen or the like 115 handled inside the safety cabinet 100 does not leak from the safety cabinet outer wall 100a, the airtightness test is defined in the standard of safety cabinet, JIS K3800 and US NSF/ANSI 49. In the airtightness test, when using the safety cabinet 100, the opened part is closed with a test cover, and the inside is pressurized with a predetermined pressure to check that there is no leakage from the outer wall, thereby proving that the pathogen or the like 115 does not leak from the safety cabinet outer wall 100a in the usage condition in which the blow-off blower 111 and the exhaust blower 112 of the safety cabinet are operated.

The suction side of the blow-off blower 111, the front panel 104, and the exhaust port 114 of the safety cabinet 100 are sealed using a cover 121 for airtightness test. When the blow-off blower 111 is covered with a cover for design of the safety cabinet 100 and having a suction port, if the cover for design has airtightness, the suction port of the cover for design may be sealed with a test cover. After sealing is completed, as specified in the safety cabinet standard, a positive pressure maintenance method of pressurizing the inside to 500 Pa by compressed air and checking that the pressure drop after 30 minutes is within 10% is used, alternatively, by a soap method of checking that there is no foaming by applying or spraying soap water or a foam leakage detection agent to the area in which there is a risk of leakage, such as a junction of the outer wall, in the state in which the inside is pressurized to 500 Pa, thereby checking that there is no leakage on the outer wall.

Figure 9:
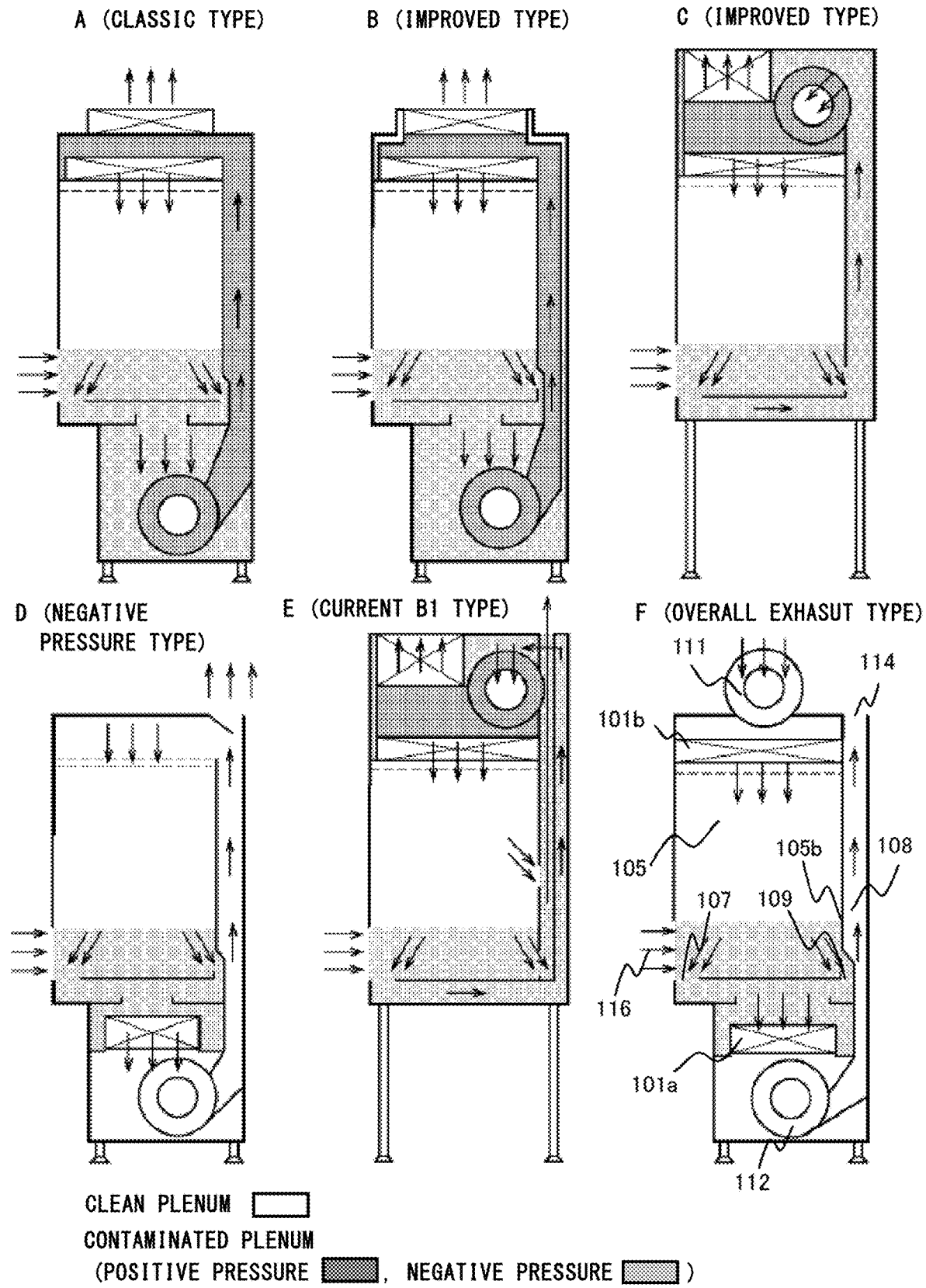
FIG. 9 is a side cross-sectional view illustrating types of safety cabinets of related art.

In the safety cabinet of related art, the non-workspace side of the workspace side wall surface 105a is the outer wall of the safety cabinet, and the non-workspace side of the workspace back wall surface 105b is the back flow path 108. Furthermore, in the safety cabinet of class II type B2 (conventional example, FIG. 9 symbol F), even if air not passing through the exhaust HEPA filter 101a leaks to the back flow path 108, it cannot be found in the airtightness test. In this example, since the workspace side wall surface 105a on both sides of the workspace 105 and the non-workspace 105 side of the workspace back wall surface 105b are formed by the safety cabinet outer wall 100a, the possibility that the pathogen or the like 115 leaks from the outer wall of the workspace 105 can be checked or eliminated by the airtightness test.

In addition, the method of evaluating that there is no possibility that the pathogen or the like may leak when using a safety cabinet from around the front panel 104 covered with the cover 121 for airtightness test at the time of airtightness test is defined in the standard of the safety cabinet as an air flow direction test.

Example 2

Figure 4A:
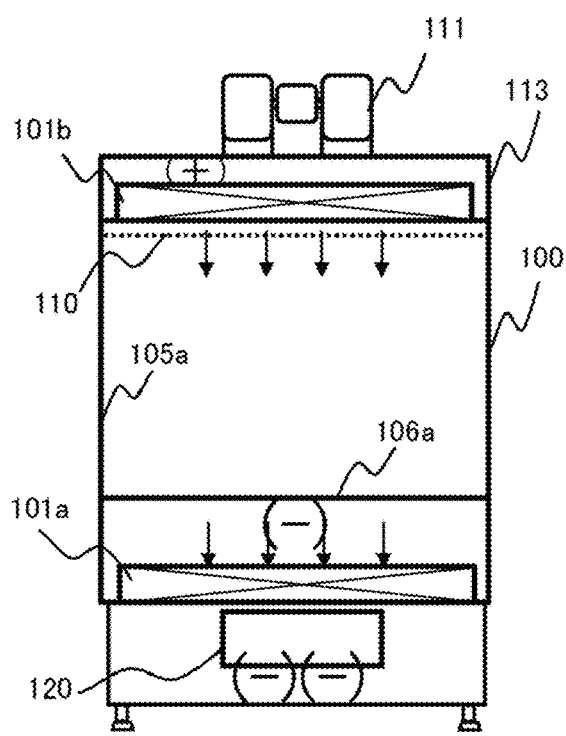
FIG. 4A is an example of a front cross-sectional view illustrating a safety cabinet of Example 2.
Figure 4B:
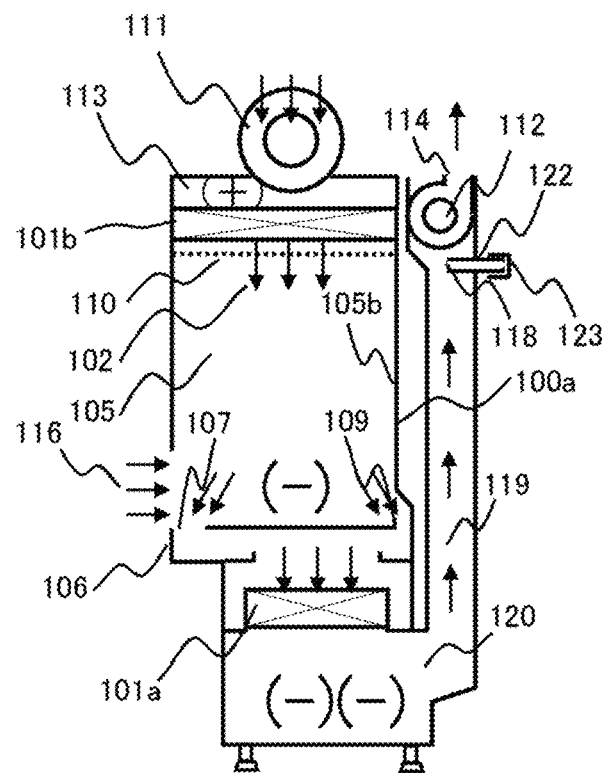
FIG. 4B is an example of a side cross-sectional view illustrating the safety cabinet of Example 2.

FIG. 4A is an example of a front cross-sectional view illustrating the safety cabinet of Example 2, and FIG. 4B is an example of a side cross-sectional view.

In Example 2, the exhaust blower 112 is provided in the exhaust flow path 119 on the downstream of the exhaust HEPA filter 101a in Example 1. The safety cabinet of Class II Type B2 of the example is always used for outdoor exhaust. The clean air 102 blown out to the workspace 105 is blown out by the blow-off blower 111, and the inflow air flow 116 is generated by the suction air flow of the exhaust blower 112. The blow-off air speed of the clean air 102 depends on the capacity of the blow-off blower 111 in the safety cabinet 100. In Example 1, the inflow air flow 116 depends on the capacity of the exhaust blower 112 installed outside the safety cabinet 100, and in Example 2, the inflow air flow 116 depends on the exhaust blower 112 disposed in the exhaust flow path 119 of the safety cabinet 100. Therefore, in Example 2, the blow-off air speed of the clean air 102 and the air speed of the inflow air flow 116 are evaluated by the safety cabinet 100 alone, and the external static pressure at the exhaust port 114 can be handed over to the exhaust system of the installation place in the state of 0 Pa. This enables the separation of responsibility in maintaining the performance of the safety cabinet 100.

In FIG. 4B, a penetration ratio measurement tube 122 having a penetration ratio measurement hole 118 is provided on the suction side of the exhaust blower 112 in which the air blown out of the exhaust HEPA filter 101a is well mixed in the exhaust flow path 119, and a penetration ratio measurement tube cap 123 is provided on the opposite side of the penetration ratio measurement hole 118. At the time of the penetration ratio test, by removing the penetration ratio measurement tube cap 123, and by taking the air into the penetration ratio detector (not illustrated), the penetration ratio test can be performed at a representative point at which the air specified by the manufacturer is well mixed.

Example 3

Figure 5A:
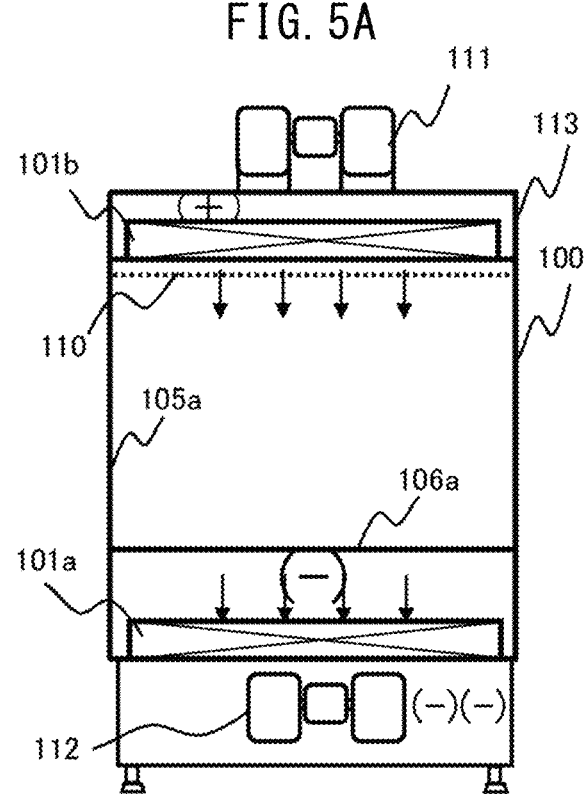
FIG. 5A is an example of a front cross-sectional view illustrating a safety cabinet of Example 3.
Figure 5B:
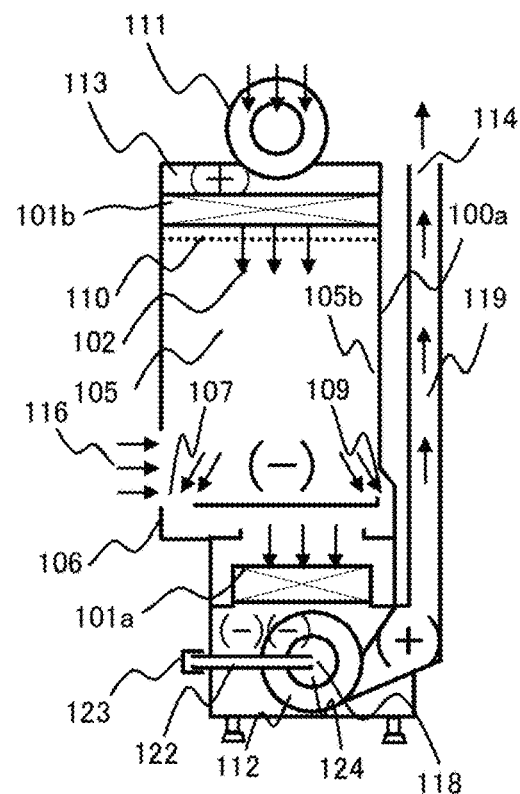
FIG. 5B is an example of a side cross-sectional view illustrating the safety cabinet of Example 3.

FIG. 5A is an example of a front cross-sectional view illustrating the safety cabinet of Example 3, and FIG. 5B is an example of a side cross-sectional view.

In Example 3, as in Example 1, an exhaust HEPA filter 101a is disposed below a work table 106. On the downstream side of the exhaust HEPA filter 101a, an exhaust blower 112 is disposed below the work table 106, and an exhaust flow path 119 is provided on the blow-off side of the exhaust blower 112. When the penetration ratio of the exhaust HEPA filter 101a is measured in Example 3, it is difficult to carry out a scanning test on the blow-off surface of the exhaust HEPA filter 101a as in other examples. In this case, it is necessary to evaluate the penetration ratio of 0.005% or less, by taking a place in which the air blown out from the exhaust HEPA filter 101a is well mixed together as a representative point. However, an exhaust blower suction port 124 which is a suction port of air of the exhaust blower 112 is a place in which the air from all the positions on the surface of the exhaust HEPA filter 101a gathers, and is the most suitable place as a representative point. In Example 3, a penetration ratio measurement hole 118 of a penetration ratio measurement tube 122 is disposed near an inlet such as the facing surface of the inlet or on an inlet circumference of the exhaust blower suction port 124, and a detachable penetration ratio measurement tube cap 123 is disposed on the opposite side of the penetration ratio measurement hole 118 of the penetration ratio measurement tube 122.

When measuring the penetration ratio of the exhaust HEPA filter 101a, by applying a load to the upstream side of the exhaust HEPA filter 101a, and by removing the penetration ratio measurement tube cap 123 and connecting it to a penetration ratio detector (not illustrated), it is possible to reliably take in the air from the exhaust HEPA filter 101a in a mixed state into the penetration ratio detector.

According to this example, since the exhaust blower 112 is disposed in the safety cabinet 100, it is possible to deliver the air to an exhaust system on a building side with an external static pressure of 0 Pa as in Example 2.

Further, in FIG. 5B, in order to use the air that mixes well on the suction side of the exhaust blower 112, the exhaust flow path 119 on the blow-off side of the exhaust blower 112 may or may not be provided in the safety cabinet 100.

Example 4

Figure 6A:
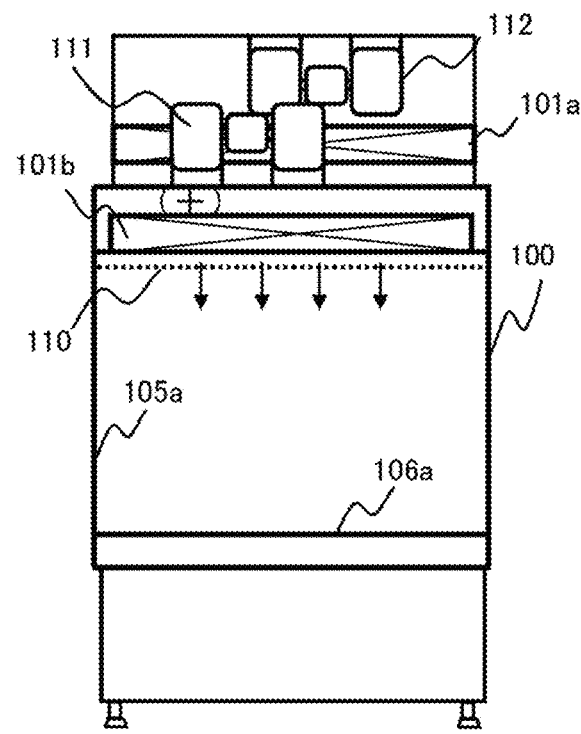
FIG. 6A is an example of a front cross-sectional view illustrating a safety cabinet of Example 4.
Figure 6B:
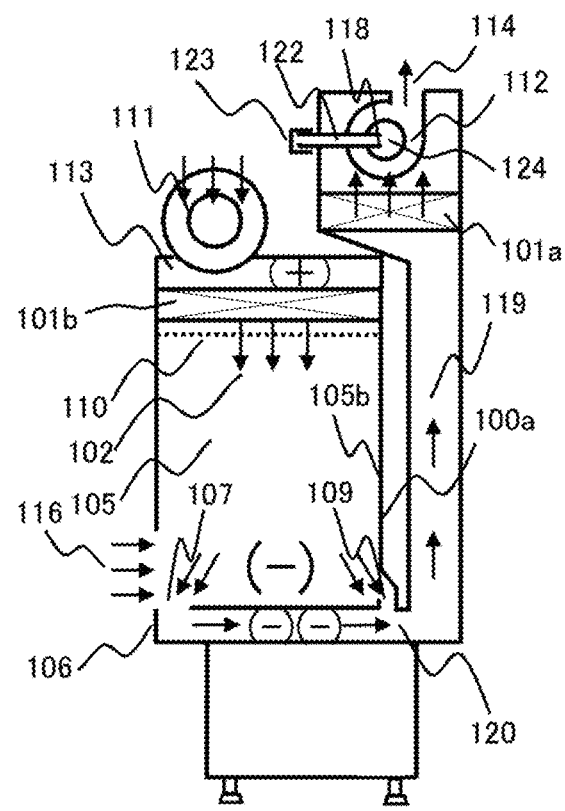
FIG. 6B is an example of a side cross-sectional view illustrating the safety cabinet of Example 4.

FIG. 6A is an example of a front cross-sectional view illustrating the safety cabinet of Example 4, and FIG. 6B is an example of a side cross-sectional view.

In this example, as in other examples, the non-workspace side of the workspace back wall surface 105b is formed by the safety cabinet outer wall 100a. In Example 4, the exhaust HEPA filter 101a is disposed above the workspace 105. Air that may contain the pathogen or the like 115 sucked from the work table front suction port 107 and the rear suction port 109 of the work table 106 passes through the exhaust flow path inlet 120 and the exhaust flow path 119, and is guided to the exhaust HEPA filter 101a. An exhaust blower 112 is disposed on the downstream side of the exhaust HEPA filter 101a, and the air from which the pathogen or the like 115 has been removed is exhausted from the exhaust port 114.

The penetration ratio measurement hole 118 of the penetration ratio measurement tube 122 is disposed in the vicinity of the inlet such as a surface facing the inlet or on the inlet circumference of the exhaust blower suction port 124 of the exhaust blower 112, and the detachable penetration ratio measurement tube cap 123 is disposed on the opposite side of the penetration ratio measurement hole 118 of the penetration ratio measurement tube 122. At the time of the penetration ratio test, the penetration ratio of the penetration ratio measurement hole 118 is measured as a representative point in which the air from the exhaust HEPA filter 101a is well mixed.

According to the present example, since the blower, the HEPA filter, and the like are not disposed below the work table 106, by maintaining the airtightness on the bottom of the work table 106, it is possible to obtain a structure in which components below the work table 106 can be easily disassembled. This structure is advantageous when the loading height at the time of loading the device is made versatile.

Figure 7:
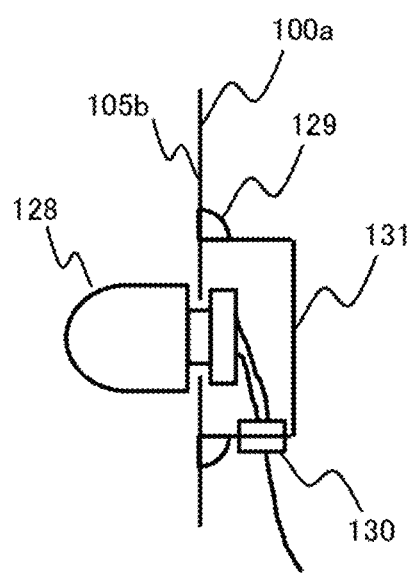
FIG. 7 is an example of a structural view of electrical components in a workspace.

FIG. 7 is an example of a structural view of the electrical components in the workspace. In common with the Examples 1 to 4, there are cases where components are attached by connecting electrical wiring from the workspace 105 such as a germicidal lamp socket and a socket to the workspace back wall surface 105b. In that case, it is necessary to provide an opening section connected to the outside of the safety cabinet 100 in the workspace back wall surface 105b for the convenience of component attachment and wiring.

When the socket 128 inside the workspace 105 is wired from the outside of the safety cabinet, the opening section for the socket 128 is covered with the outer wall cover 131. The outer wall cover 131 is provided with a wiring connector 130. As the wiring connector 130, one having airtightness is commercially available. The outside of the safety cabinet 100 and the socket 128 are wired, using the wiring connector 130. The place in which the outer wall cover 131 and the safety cabinet outer wall 100a are in contact with each other is secured its airtightness by a caulking material 129, such that it is possible to maintain the airtightness required for the safety cabinet. This method is also applied to the case of the workspace side wall surface 105a.

Example 5

Figure 8A:
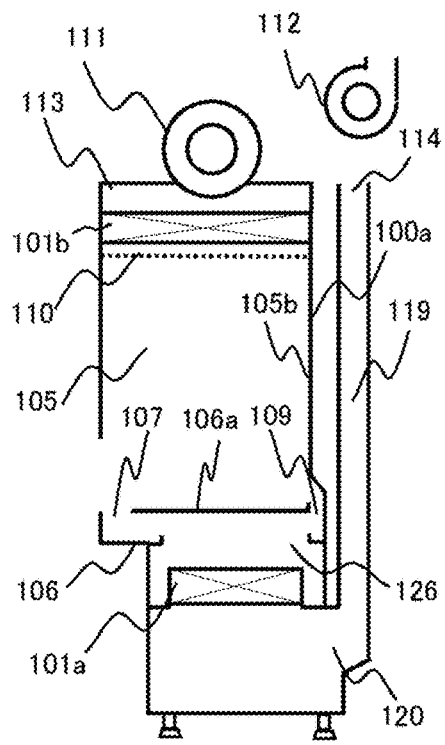
FIG. 8A is an example of a side cross-sectional view illustrating a safety cabinet of Example 5.
Figure 8B:
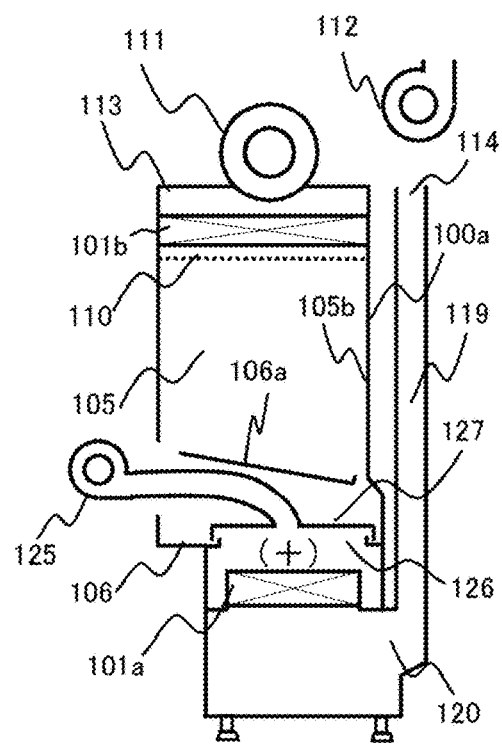
FIG. 8B is an example of a side cross-sectional view at the time of a penetration ratio test illustrating a safety cabinet of Example 5.

FIG. 8A is an example of a side cross-sectional view illustrating the safety cabinet of Example 5, and FIG. 8B is an example of a side cross-sectional view at the time of penetration ratio test.

When measuring the penetration ratio of the HEPA filter 101, it is necessary to measure the concentration of simulated dust of both the upstream and downstream sides of the HEPA filter, and to divide the downstream side concentration by the upstream side concentration. In order to calculate the penetration ratio of 0.01% or less and 0.005% or less, it is necessary to sufficiently increase the simulated dust concentration of the upstream side. In that case, it is necessary to increase the supply amount of simulated dust to the upstream side. In the case of measuring the penetration ratio of the blow-off HEPA filter 101b, it is possible to input the simulated dust using the pressure of the blow-off blower 111 and fill the inside of the pressure chamber 113. However, when there is no blower or pressure chamber on the upstream side of the exhaust HEPA filter 101a, it is necessary to input the simulated dust into the workspace 105 from the work opening section 103 with the test blower 125 and to increase the simulated dust concentration on the upstream side of the exhaust HEPA filter 101a. However, in this case, since the simulated dust is filled inside workspace 105 used for the experiment, and the simulated dust adheres to the inner wall surface of the workspace 105, the inside of the workspace 105 needs to be cleaned after the penetration ratio test.

In general, the safety cabinet has a structure in which the work table 106 below the work surface 106a can store liquid for the convenience of putting a disinfecting solution or the like to perform disinfection. Therefore, the workspace side around the opening section of the work table lower opening section 126 has a protrusion for blocking water. In addition, the work surface 106a is detachable in order to make the lower part of the work surface 106a cleanable.

In Example 5, the work surface 106a is lifted as illustrated in FIG. 8B, and the protrusion around the work table lower opening section 126 is covered with a penetration ratio test cover 127 to seal the space in which the exhaust HEPA filter 101a is disposed. The penetration ratio test cover 127 is provided with an opening section to which the blow-off port of the test blower 125 can be connected. By suctioning the simulated dust for penetration ratio test from the test blower 125, the upstream side of the exhaust HEPA filter 101a can be pressurized with air containing the simulated dust, and can be raised to an upstream concentration sufficient for measurement. In the present example, since only the space around the exhaust HEPA filter 101a below the work table 106 is contaminated by the simulated dust, it is possible to prevent the inside of the workspace 105 from being contaminated by the simulated dust. The concentration measurement method on the downstream side of the exhaust HEPA filter 101a is the same as in other examples.

According to Example 1 to 5, in the safety cabinet in which it is difficult to perform the penetration ratio test by the scanning test of the exhaust HEPA filter, it is possible to provide a safety cabinet which facilitates checking of penetration ratio and eliminates the possibility of pathogen or the like leaking from the outer wall of the workspace. In addition, since the test method and the air flow condition at the time of the test are in the state of the same air flow at the time of shipment by the safety cabinet manufacturer and at the site inspection performed regularly, evaluation can be made by the same measurement sensitivity at the time of shipment by the safety cabinet manufacturer and at the site inspection.

Although the safety cabinet standard of JIS K3800: 2009 describes the penetration ratio test method using a relative densitometer (photometer), in the examples, the same also applies to a case in which the dust concentration on the upstream side of the HEPA filter and the dust concentration on the downstream side of the HEPA filter are measured and compared, using a light scattering type automatic particle counter (a particle counter).

REFERENCE SIGNS LIST

100 Safety cabinet
100a Safety cabinet outer wall
101a Exhaust HEPA filter
101b Blow-off HEPA filter
102 Clean air
103 Work opening section
104 Front panel
105 Workspace
105a Workspace side wall surface
105b Workspace back wall surface
106 Work table
106a Work surface
107 Work table front suction port
108 Back flow path
109 Rear suction port
110 Flow straightening plate
111 Blow-off blower
112 Exhaust blower
113 Pressure chamber
114 Exhaust port
115 Pathogen or the like
116 Inflow air flow
118 Penetration ratio measurement hole
119 Exhaust flow path
120 Exhaust flow path inlet
121 Airtightness test cover
122 Penetration ratio measurement tube
123 Penetration ratio measurement tube cap
124 Exhaust blower suction port
125 Test blower
126 Work table lower opening section
127 Penetration ratio test cover
128 Socket
129 Caulking material
130 Wiring connector
131 Outer wall cover

The invention claimed is:
1. A safety cabinet comprising:
a work surface on a bottom of a workspace;
a front panel at a front of the workspace;
a work opening section below the front panel;
a first air filter configured to filter exhaust air for exhausting air in the workspace,
an outer wall forming non-workspace sides of a side wall surface and a back wall surface of the workspace;
an opening section below the work surface at the bottom of the workspace;

a penetration ratio test cover which covers the opening section and seals a space in which the first air filter is disposed; and a test blowing unit connected to the penetration ratio test cover.

* * * * *